United States Patent
Loock et al.

(10) Patent No.: US 7,483,598 B2
(45) Date of Patent: Jan. 27, 2009

(54) PHASE SHIFT OPTICAL LOOP SPECTROSCOPY

(75) Inventors: Hans-Peter Loock, Kingston (CA); Zhaoguo Tong, Kitchener (CA)

(73) Assignee: Queen's University at Kingston, Kingston, Ontario (CA)

(*) Notice: Subject to any disclaimer, the term of this patent is extended or adjusted under 35 U.S.C. 154(b) by 0 days.

(21) Appl. No.: 11/079,478

(22) Filed: Mar. 15, 2005

(65) Prior Publication Data

US 2005/0201661 A1  Sep. 15, 2005

Related U.S. Application Data

(60) Provisional application No. 60/552,709, filed on Mar. 15, 2004.

(51) Int. Cl.
*G02B 6/00* (2006.01)

(52) U.S. Cl. ....................................................... 385/12
(58) Field of Classification Search ........................ None
See application file for complete search history.

(56) References Cited

U.S. PATENT DOCUMENTS

| | | | | |
|---|---|---|---|---|
| 5,208,652 | A * | 5/1993 | Sonobe et al. | 356/460 |
| 6,097,487 | A * | 8/2000 | Kringlebotn et al. | 356/450 |
| 6,842,548 | B2 | 1/2005 | Loock et al. | |
| 2002/0048422 | A1 * | 4/2002 | Cotteverte et al. | 385/4 |
| 2002/0131737 | A1 * | 9/2002 | Broeng et al. | 385/123 |
| 2004/0061863 | A1 * | 4/2004 | Digonnet | 356/460 |
| 2004/0118977 | A1 | 6/2004 | Lehmann et al. | |

OTHER PUBLICATIONS

Engeln, R., et al., "Phase shift cavity ring down absorption spectroscopy." *Chem. Phys. Lett.* 262: 105-109 (1996).
Stewart, G., et al., "An investigation of an optical fibre amplifier loop for intra-cavity and ring-down cavity loss measurements." *Meas. Sci. Technol.* 12: 843-849 (2001).
Wang, C., et al., "Fiber loop ringdown for physical sensor development: pressure sensor." *Applied Optics* 43: 6458-6464 (2004).
Wang, C., "Fiber ringdown temperature sensors." *Optical Engineering* 44 (2005).

* cited by examiner

*Primary Examiner*—Sung H Pak
*Assistant Examiner*—Hoang Tran
(74) *Attorney, Agent, or Firm*—Stephen J. Scribner

(57) ABSTRACT

The invention provides a method and apparatus for measuring one or more optical properties, such as absorbance and refractive index, of a test medium such as a gas, a liquid, or solid material. The method comprises providing a passive optical waveguide loop comprising the test medium, launching in the optical loop an intensity-modulated light at a reference phase, detecting a phase of said light along the optical waveguide loop, and comparing the detected phase of said light along the loop with the reference phase, wherein the comparison provides information about one or more optical properties of the test medium.

14 Claims, 9 Drawing Sheets

PHASE SHIFT OPTICAL LOOP SPECTROSCOPY

RELATED APPLICATIONS

This application claims the benefit of the filing date of U.S. Provisional Patent Application No. 60/552,709, filed on Mar. 15, 2004, the contents of which are incorporated herein by reference in their entirety.

FIELD OF THE INVENTION

This invention relates to methods and apparatus for measuring optical characteristics of a test medium or media. In particular, the invention relates to use of the phase shift of light in an optical loop to measure optical characteristics of a test medium or media.

BACKGROUND OF THE INVENTION

Measurement of low optical losses of an absorbing medium, such as a gas or a molecular beam, may be performed by measuring the ring-down time, or decay time, of a light pulse as the pulse makes multiple passes through the medium. Such measurements may be carried out in a ring-down cavity consisting of two or more mirrors, between which the light pulse is reflected, and in which the absorbing medium under test is disposed. The cavity can also be used to characterize the mirrors when no absorbing medium is present. See, for example, Romanini et al., 1993; Scherer et al., 1997; Berden et al., 2000; Lehmann, U.S. Pat. No. 5,528,040, issued Jun. 18, 1996.

Cavity ring-down spectroscopy (CRDS) is well established as a gas phase measurement method. Recently CRDS was shown to be applicable to absorption measurements on liquid samples, in which a high finesse cavity was either filled entirely with a liquid sample (Hallock et al., 2002) or the liquid was contained in a cuvette (Xu et al., 2002).

Ring-down spectroscopy using optical fibers rather than a cavity was attempted by von Lerber et al. (2002), who deposited highly reflective coatings onto both end facets of a 10 m optical fiber. Stewart et al., (2001) inserted a gas phase absorption cell into a fiber-loop, leading to very high transmission losses. These losses necessitated the use of a fiber amplifier, and the sensitivity of measurements using such an active loop depended strongly on the amplifier's temporal stability.

We have previously demonstrated a fiber-loop ring-down technique for characterizing low-loss processes in optical systems and for spectroscopy of minute liquid samples (Loock et al., U.S. Pat. No. 6,842,548, issued Jan. 11, 2005), based on measuring the ring-down time of a light pulse injected into the loop. Although extremely sensitive, limitations of that technique include slow data acquisition rate and high cost of optical components such as fast pulsed lasers.

SUMMARY OF THE INVENTION

According to one aspect of the invention there is provided a method for measuring one or more optical properties of a test medium, comprising: providing an optical waveguide loop comprising a test medium; launching in the optical waveguide loop intensity-modulated light at a reference phase; detecting a phase of said light along the optical waveguide loop; and comparing the detected phase of said light along the loop with the reference phase; wherein comparing the detected phase and the reference phase provides information about one or more optical properties of the test medium.

In a preferred embodiment, the optical waveguide loop is passive. In another preferred embodiment, the optical waveguide is an optical fiber. In various embodiments, the optical waveguide loop is the test medium, or the optical waveguide loop comprises a capillary channel for said test medium.

In another embodiment, the test medium is exposed to an evanescent wave of light that is guided by the optical waveguide loop. In a further embodiment, the optical waveguide loop comprises a cladding, and the test medium is in the cladding.

In one embodiment, the optical property is absorbance. In various embodiments, the light has at least one wavelength selected from infra-red (IR), visible, and ultra-violet. The light may have a wavelength selected from about 200 nm and 2000 nm, preferably about 200 nm to about 1700 nm. The test medium may be selected from a gas, a molecular beam, a liquid, and a solid material. In a preferred embodiment, the test medium is a liquid.

In another embodiment, the optical waveguide loop comprises a single-mode optical fiber, and the method comprises launching in the optical waveguide loop a single longitudinal mode of an intensity-modulated light; wherein the phase of the longitudinal mode is indicative of one or more optical properties of the test medium. In a further embodiment, the method further comprises measuring intensity of said longitudinal mode.

In another embodiment, the test medium comprises a mechanical sensor for receiving a mechanical force, and the one or more optical properties of the test medium provide information about the mechanical force received by the mechanical sensor. The mechanical force may be selected from stress and strain.

According to another aspect of the invention there is provided an apparatus for measuring one or more optical properties of a test medium, comprising: an optical waveguide loop comprising a test medium; an intensity-modulated light source for illuminating the loop with light at a reference phase; a detector for detecting a phase of said light along the loop; and an analyzer for comparing the detected phase of the light with the reference phase of the light; wherein the comparison is indicative of one or more optical properties of the test medium. The analyzer may output a result of the comparison, wherein the result is indicative of one or more optical properties of the test medium.

In one embodiment, the apparatus further comprises a device for displaying and/or storing and/or manipulating data corresponding to at least one of said reference phase, said detected phase, and said comparison.

In a preferred embodiment, the optical waveguide loop is passive. In various embodiments, the optical waveguide loop is an optical fiber or a single-mode optical fiber. In a further embodiment, the optical waveguide loop is the test medium. In some embodiments the apparatus further comprises a capillary channel for guiding the test medium to said light.

In another embodiment, test medium is exposed to an evanescent wave of light that is guided by the optical waveguide loop. In some embodiments, the optical waveguide loop comprises a cladding, and the test medium is in the cladding. In further embodiments, the test medium or the optical fiber comprises a grating.

In various embodiments, the optical property is absorbance, and in other embodiments, light has at least one wavelength selected from infra-red (IR), visible, and ultra-violet.

The wavelength may be between about 200 nm to 2000 nm, preferably between about 200 nm to 1700 nm.

In one embodiment, the apparatus comprises a microfluidic device.

In another embodiment, the test medium comprises a mechanical sensor for receiving a mechanical force, and the one or more optical properties of the test medium provide information about the mechanical force received by the mechanical sensor. The mechanical force may be selected from stress and strain.

BRIEF DESCRIPTION OF THE DRAWINGS

Embodiments of the invention are described below, by way of example, with reference to the accompanying drawings, wherein.

DETAILED DESCRIPTION OF THE PREFERRED EMBODIMENTS

Figure 1:
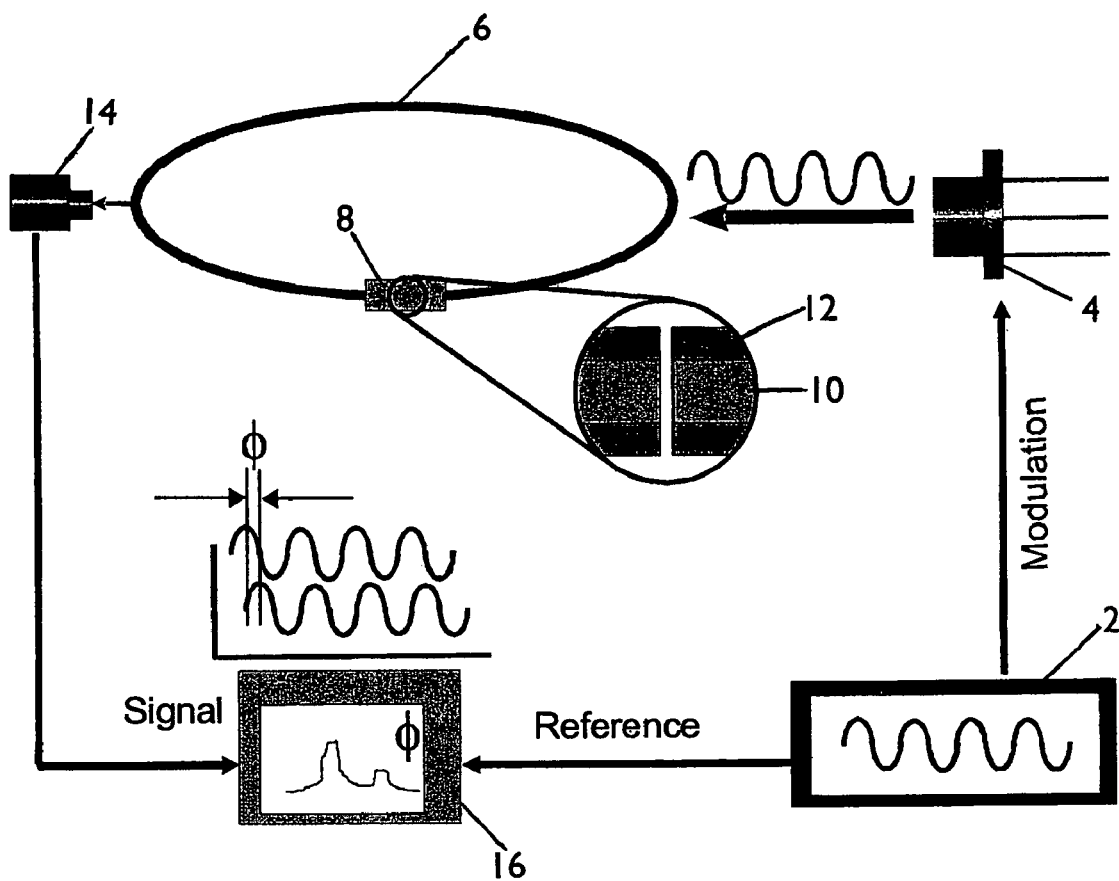
FIG. 1 is a block diagram of a phase shift fiber loop system according to the invention for measuring optical properties of an optical fiber and connector.

Engeln et al. (1996) measured the phase shift associated with an optical decay in cavity ring-down spectroscopy (CRDS) and observed that, due to the greatly enhanced duty cycle, the accuracy of the technique compared favourably with pulsed CRDS. To our knowledge, phase shift CRDS (PS-CRDS) has been used only once since 1996, when Lewis et al. (2001) reported on the $\Delta v=6$ vibrational overtone transitions of different hydrocarbons. DeMille et al. (2002) later compared these measurements with overtone spectra obtained using conventional CRDS and intracavity laser photoacoustic spectroscopy and noted that PS-CRDS yields absorption cross sections about 35% higher than those obtained with either of the conventional techniques, possibly indicating systematic errors in the PS-CRDS system. The lack of interest in PS-CRDS is likely due to its shortcomings, which include the inability to deal with multiple exponential decays, mode-beating, sensitivity to electrical and optical noise, and difficulty of measuring small phase angles in 1 MHz oscillations.

We nevertheless believe that the phase shift technique in general offers a major advantage over pulsed (time-resolved) CRDS, in that the time response of measurements is vastly improved. We believe that the fast time response of the technique is of particular relevance to liquid phase spectroscopy of very small samples that can be changed or cycled rapidly, where measurement time becomes the limiting factor in sample throughput. Also, there may be other sources of optical loss that change quickly and can not readily be sampled using the conventional pulsed CRDS technique. Such losses could, for example, be due to fast chemical processes or mechanical modifications to the cavity geometry.

This invention is based, in part, on the recognition that the advantage of the phase shift technique may be exploited when adapted to a measurement method employing an optical wave guide loop. Prior to the invention, such spectroscopic techniques could not be carried out on very small liquid phase samples, and for gas phase measurements, the fast time response was not important enough to offset the drawbacks of the technique. Although Stewart et al. (2001) suggested that a phase shift technique might be applied to a measurement method employing an optical fiber loop, that suggested method used a microoptic gas cell having high loss (1 dB), and hence required an amplifier in the loop. As a result, the technique suggested by Stewart et al. (2001) did not involve a passive loop. Moreover, the suggested technique would be complex and expensive to implement, and would be vulnerable to complications such as gain control and amplifier stability associated with an amplified loop.

According to a broad aspect of the invention, there is provided a method of measuring one or more optical properties of a test medium by measuring the phase shift of light traveling around an optical waveguide loop and through the test medium. The invention provides a method by which the phase shift of light in a waveguide loop can be used in characterizing the optical properties of a test medium. Preferably, the optical waveguide loop is passive, meaning that the loop does not have a device (e.g., an amplifier) for amplifying light.

As used herein, the terms "change in phase", "phase change", "phase shift", and "phase angle difference" are equivalent and refer to a change in the phase $\phi$ of an optical signal as a function of the test medium through which the signal travels. A change in phase may be considered as a temporal shift in a light signal waveform (the waveform having a period of 360 degrees) after passing through a test medium, relative to a reference. The reference may be, for example, the phase of the light signal prior to passing through the test medium. For convenience, the reference phase (e.g., phase of the light signal entering the optical waveguide) may be designated as 0 degrees, and the phase change of the light signal after passing through the test medium (e.g., phase of the light signal exiting the optical waveguide) may be expressed relative to 0 degrees.

As used herein, the term "test medium" is intended to mean any medium or material the optical properties of which can be measured in accordance with the invention. The test medium is exposed to at least a portion of the light that is guided by the optical waveguide, wherein that portion of light is either within the waveguide, or outside of the waveguide (i.e., the evanescent wave). Examples of test media include, but are not limited to, the optical waveguide loop itself, a portion of a second optical waveguide inserted into the loop, a modified optical waveguide, an optical connector or an optical device (e.g., a grating or filter), a sample of a gas, liquid, or solid material (e.g., a film or coating, such as a solid or liquid film deposited on the facet end of an optical fiber), a molecular beam, or a stationary test medium. Samples of gases and liquids may be introduced into the loop using a small conduit for conducting the sample therethrough, the conduit intersecting the loop in a manner that allows all or a portion of the light to pass through the sample. For example, the conduit may be a tube, such as a capillary tube (i.e., a "capillary"), or a flow channel, which may also be referred to as a capillary channel or a capillary flow channel. The flow channel may be etched or machined into a substrate. It will be appreciated that flow of a sample through such a conduit may or may not involve capillary action. Where flow does not involve capillary action, flow may be established using any technique known in the art, such as a pump, an electrical and/or chemical gradient, a pressure differential, or the like. A test medium may also be introduced to the optical waveguide loop so as to intercept at least a portion of the evanescent wave. In the case where an optical fiber is used for the optical waveguide, this may be achieved by, for example, modifying a portion of the fiber cladding to accommodate a test medium. For example, a portion of the fiber cladding may be removed to expose a test medium to the evanescent wave that resides in the cladding close to the interface of the cladding and the fiber core.

As used herein, the term "optical properties" is intended to mean any property of a medium that is light-dependent. Examples of optical properties are absorbance, scattering efficiency, refractive index, evanescent wave spectrum, and optical loss. Optical properties are indicative of, or related to, physical and/or chemical characteristics of a medium (e.g., density, structure (such as 1-, 2-, or 3-dimensional structure)). Thus, in accordance with the invention, one or more optical properties of a medium is/are indicative of one or more physical and/or chemical characteristics of the medium.

As used herein, the term "optical waveguide" is intended to encompass any conduit for light. An optical waveguide according to the invention is capable of being formed into or provided as a continuous loop, e.g., by joining the two ends of the waveguide together, such that a light signal launched in the waveguide travels around the loop repeatedly. Thus, as used herein, the term "optical waveguide loop" refers to a loop made of an optical waveguide. The loop is continuous insofar as it provides a continuous path for a light signal travelling therethrough; however, the loop may have an opening into which a test medium may be inserted. Examples of optical waveguides are optical fibers, such as those having a solid core, hollow core (i.e., capillary fiber), or liquid core, and waveguides based on high refractive index fluids. Optical waveguides can also be prepared on a substrate such as glass or polymeric material, for example, in embodiments where the invention comprises a microchip. Where optical fiber is employed, such fiber may be selected from commercially available fibers, including multi-mode and single mode fibers. The two ends of waveguides such as optical fibers are joined using splice connectors, such as any commercially available connector, fusion spliced connections, or any other suitable technique known in the art. Preferably, such fibers and connections have low transmission loss (e.g., absorbance, geometrical mismatch, scattering). In this regard, waveguides based on high refractive index fluids are advantageous in that such connectors are not required.

In accordance with the invention, the optimum length of the optical waveguide loop depends on the desired measurement sensitivity and detection limit. Generally, as optical losses within the loop decrease, the loop may be made shorter. For very small losses, the loop is preferably as short as possible. In a typical measurement scenario, such optical losses would be caused by absorption of the test medium. It is expected that for certain applications an entire apparatus according to the invention may be fabricated on a microchip. In practice, the minimum length of the loop may be limited by factors that contribute to loss of the light signal, such as a small radius of the bend in the waveguide (loss increases as radius decreases), high loss of a waveguide splice (e.g., a fiber optic splice connector), or high absorbance of a test medium. Loop length is discussed in detail in Jakubinek et al. (2004). It should be noted that in forming the loop, the optical waveguide can be "wound" into any shape, as may be required for compactness, etc., of the loop. This is of relevance especially when long loops are required.

It is preferred that the optical waveguide loop is a passive loop. As used herein, the term "passive loop" refers to a loop that does not have a device (e.g., an amplifier) for amplifying light.

In accordance with the invention, the light signal may be of any wavelength from about 2000 nm to about 200 nm (i.e., infra-red (IR) to ultra violet (UV)), preferably from about 1700 nm to about 200 nm. However, use of wavelengths longer than 1700 nm may be problematic due to the high transmission losses in typical waveguide materials (e.g., silica). Use of UV may also be problematic because of the degradative effects of UV light on optical materials, and comparatively high losses (e.g., 1% per m of optical fiber). However, UV is of particular interest in chemical, biochemical, biological, and environmental studies, because many compounds and substances of interest absorb in this wavelength. In some embodiments of the invention the light signal has a narrow bandwidth (e.g., a single colour of light), whereas in other embodiments, the light signal is wide band (e.g., white light). Suitable light sources are those light sources capable of being modulated at a rate that is comparable to $1/\tau$, where $\tau$ is the optical decay constant of the waveguide loop. The light source may be, for example, a laser, a laser diode, or a light emitting diode (LED). In embodiments employing a spectroscopic approach wherein ring-down time as a function of wavelength is sought, a tunable laser can be employed, and such laser swept to produce laser radiation over a range of wavelengths. The light signal may be coupled into the waveguide using any conventional approach or device, such as, for example, a directional coupler. However, in the case of optical fiber, light may be coupled into the fiber simply by illuminating the fiber. When using a 1 W laser, the inventors achieved good coupling of light into an optical fiber by first focussing the laser light into a power delivery fiber, and then connecting this fiber to the loop using a drop of DMSO solvent, which acted as index matching fluid. When using a 10 mW infrared laser at 1600 nm, low loss was achieved using a 99.5%:0.5% directional coupler, despite the fact that the coupler introduced a considerable (4%) insertion loss of light per pass around the loop. Using evanescent coupling (Polynkin et al., 2004) these insertion losses were further reduced and coupling efficiency was further optimized.

One embodiment of the invention is shown in FIG. 1. In this embodiment, a function generator 2 modulates the intensity of light from a source such as a laser 4. The modulated light signal is coupled into an optical wave guide, in this case an optical fiber 6, which is formed into a loop using a fiber splice connector 8. As shown in the inset, the optical fiber comprises a core 10 and cladding 12. The light signal traveling through the fiber loop is detected using a photon detector 14. The detected light may be displayed on a suitable device such as an oscilloscope, while the phase angle difference between the light entering and exiting the fiber 6 may be determined, for example, by a lock-in amplifier 16 or a ratiometer. The data may be stored in and/or analyzed by a computer. By measuring the phase angle with respect to a suitable reference such as the phase of the incoming modulated light (see FIG. 2), various loss mechanisms of the test medium can be characterized. Advantageously, such losses are largely independent of power fluctuations of the light source. Thus, unlike conventional single or multipass-type devices, the invention is not sensitive to the intensity of the input light signal, to the input coupling efficiency of the light signal, or to drift of the light signal power with, for example, time, temperature, or wavelength. The method of the invention is not very sensitive to laser alignment, and a long loop can be provided to allow for spatially separate illumination and detection regions.

In a preferred embodiment, the invention comprises launching a modulated continuous light signal into the optical loop, and recording the phase angle over a time constant corresponding to a number of oscillation cycles (i.e., periods or wavelengths) of the modulated light signal being averaged. Use of a larger time constant increases the number of oscillation cycles averaged, and hence provides a more accurate measure of the phase angle difference. Use of a lock-in amplifier conveniently provides for adjustment of the time constant.

The embodiment shown in FIG. 1 is suitable for applications such as characterizing loss processes in fiber optic transmission. For example, the method can be used to accurately determine the absolute transmission spectrum of an optical fiber and of the fiber connector, as well as other optical properties such as refractive index, evanescent wave spectrum, and optical loss. Further, the deformation (e.g., strain) of a fiber can be evaluated by determining the effect of the deformation on one or more such optical properties of the fiber. Deformation may be caused by a mechanical force (e.g., stress), and/or by physical factors (e.g., temperature, pressure) acting on the fiber. For example, deformation may comprise bending the fiber, with a smaller radius of the bend associated with greater deformation, and hence greater changes of optical properties of the fiber.

In one embodiment, the invention is used to measure one or more optical properties (e.g., absorbance) of a test medium, using a short optical path length through the test medium (e.g, a path length less than about 100 μm, preferably about 1 to 10 μm). A short optical path length can be achieved by using a very small capillary channel to introduce the test medium (such as a liquid or a gas) into the loop, for example. It will be appreciated that this embodiment requires only very small sample volumes of test medium (e.g., in the order of picoliters).

In particular, the invention is advantageously used in spectrometry of small volumes of test media such as fluid (i.e., liquid or gas) samples. It is desirable to measure very small samples of a substance, particularly when the substance is expensive, rare, or toxic. However, previously-known cavity techniques are not conveniently applied to measurement of very small samples because of the larger sample quantities generally required. Further, use of small sample volumes in accordance with the invention makes possible rapid flushing of the channel, and hence a high repetition rate for measurement of subsequent samples (e.g., less than 1 s for a measurement). Previously known cavity techniques cannot provide such rapid flushing of samples because of the large samples required, and hence cannot provide rapid measurement of successive samples. Previously known ring-down spectroscopy techniques, even when applied to measurement of small samples in capillary channels, cannot provide rapid measurement of successive samples because of the considerable time required for data acquisition and processing. Thus, none of the above-mentioned techniques provides rapid measurement of optical properties of very small fluid samples of test media.

The phase shift optical loop method of the invention provides for an extremely sensitive and rapid absorption spectroscopic technique, and as such it is suitable for numerous applications, as exemplified by the embodiments described below. It is noted that, in contrast to most other absorption measurement techniques, the sensitivity of the phase angle measurement (i.e., the change of phase angle with concentration change) is larger for weak absorption processes than for strong absorption processes. Therefore, the invention is well suited to weak absorbers, dilute samples, and/or short absorption path lengths.

In another embodiment, the phase shift due to optical losses of an evanescent wave is used for example to detect the presence of one or more compounds, or to measure the absorption spectrum of one or more compounds. This embodiment takes advantage of the fact that significant optical energy resides in the cladding close to the interface with the core. In such embodiment, the fiber cladding on a section of the loop can either be removed, coated, replaced (e.g., with a chemically modified polymer, such as a silicon-based polymer), or modified (e.g., chemically), to permit detection and recording of the evanescent wave absorption spectrum produced by a compound(s) exposed to the evanescent wave. In particular, solid phase micro extraction (SPME) may be used, in which a polymer coating provides enrichment of the analyte (e.g., by 2000 times or more) through extraction of the analyte into the polymer, may be used. The partitioning coefficients that govern the efficiency of solid phase microextraction vary depending on the class of chemicals and the polymer matrix. For example, Table 1 lists a number of siloxane-based polymers and corresponding types of analytes for which they are suitable, which may be used in accordance with the invention. Partitioning of a molecule of interest into the cladding changes its optical properties (for example, refractive index, optical absorbance), resulting in a change in the reflection efficiency of the cladding and its optical losses. Effects of such changes on the evanescent wave can be measured using the phase shift techniques of the invention.

TABLE 1

Examples of siloxane-based polymers suitable for solid phase micro extraction (SPME) polymer coatings on optical fibers.

| SPME Coating | Application |
| --- | --- |
| 100 μm polydimethylsiloxane | For Volatiles |
| 7 μm polydimethylsiloxane | For Nonpolar High Molecular Weight Compounds |
| 85 μm polyacrylate | For polar semivolatiles |
| 30 μm polydimethylsiloxane | For Nonpolar Semivolatiles |
| 65 μm polydimethylsiloxane/divinylbenzene | For Volatiles, Amines, and Nitroaromatic Compounds |
| 65 μm Carbowax/divinylbenzene | For Alcohols and Polar Compounds |
| 60 μm polydimethylsiloxane/divinylbenzene | For Amines and Polar Compounds (HPLC use only) |
| 50 μm Carbowax/templated resin | For Surfactants (HPLC use only) |
| 75 μm Carboxen/polydimethylsiloxane | For Gases and Low Molecular Weight Compounds |
| 65 μm polydimethylsiloxane/divinylbenzene | For Volatiles, Amines, and Nitroaromatic Compounds |
| 50/30 μm divinylbenzene/Carboxen | For Flavor Compounds (Volatiles and Semivolatiles) |
| 85 μm Carboxen/polydimethylsiloxane | For Gases and Low Molecular Weight Compounds |
| 70 μm Carbowax/divinylbenzene | For Alcohols and Polar Compounds |
| 100 μm polydimethylsiloxane | For Volatiles |
| 50/30 μm divinylbenzene/Carboxen | For Odor Compounds |

In another embodiment, there is provided a method of measuring polarization-dependent loss using pulsed polarized laser light as a source and a polarization-maintaining fiber for the loop. Polarization-dependent loss is an important quantity in the telecommunications industry; however, such measurements are difficult to undertake with currently available technology.

According to another aspect of the invention there is provided an apparatus for measuring one or more optical properties of a test medium by measuring the phase angle difference of the modulation of light guided by the waveguide loop and passing through the test medium, relative to a reference phase angle. An example of such an apparatus is an absorbance detector.

In accordance with this aspect of the invention, the loop has a test medium introduced therein. The test medium is a material for which optical properties are to be measured. For example, where optical fiber is employed for the optical loop, the medium used for index matching in the fiber-splice may be replaced with a test medium such as water, organic solvent, etc. Typically, such test medium will have a refractive index different from the refractive index of the fiber core. In such an embodiment, the space between the two fiber ends acts as a Fabry-Perot cavity. The loss processes are then determined by the refractive index of this cavity with respect to the fiber as well as by the modes present in the fiber. It is therefore necessary to accurately determine the mode structure of the Fabry-Perot cavity and its change as a function of the refractive index of the cavity medium. Maintaining a stable mode structure in a conventional cavity ring-down laser absorption spectroscopy experiment is challenging, since the mirrors are typically spaced by tens of centimeters and the laser pulse coupled into the cavity contains a large number of modes. In this embodiment, however, the loop substantially simplifies the measurement of the cavity modes if a single mode waveguide is used.

In one embodiment, the invention provides an absorption detector wherein a test medium for absorption measurement is introduced into the optical path of the optical loop. This can be accomplished by providing the test medium in, for example, a capillary tube or channel or a flow channel, appropriately interfaced with the optical loop. For example, depending on the dimensions of the optical waveguide and the capillary, flow channel, capillary channel, or the like, the latter may either intersect the optical waveguide, or it may pass through the waveguide, via, for example, a hole through the waveguide. Further, at least a portion of the optical waveguide loop may be incorporated into a chip, such as, for example, a microfluidic device. For example, where optical fiber is employed, the splice connector may be replaced with such a microfluidic device (e.g., a "lab-on-a-chip" device). Such devices are provided with channels having cross-sections in the order of microns, for carrying small amounts of analyte solution. The solutions can be separated into their solutes in the channels. A microfluidic device thus provides a well-defined small gap between the waveguide ends. The waveguide loop intersects one such channel, thereby forming part of a sensitive, selective absorption detector. The detection limit for such a device was experimentally determined to be about $e[l/mol\ m]*c[mol/l]\ d[m]=10^{-5}$. A strongly absorbing molecule (e.g., $e=10^6$ l/mol m) can therefore be detected at concentrations of several micromoles per liter. Improvement of the detection limit may be achieved through, for example, using a lower base loss fiber connector and a low loss fiber, or by using a larger time constant for the phase angle measurement.

In a variation of this embodiment, polarization-maintaining fibers and optically active analytes are used, such that small quantities of absorbing media can be detected in a small absorption cell.

In another embodiment the fiber loop is made of single-mode optical fiber and the excitation laser has a bandwidth that is comparable to the spectral width of each mode. The fiber loop has a mode structure dependent upon the length of the loop and the diameter of the core. By selectively exciting a single longitudinal mode of the loop, the intensity of light inside the loop and of the emitted light can be increased, thereby reducing the time needed for averaging the oscillating signal.

In another embodiment optical properties such as the refractive index can be measured by selectively exciting a single longitudinal mode in a fiber loop made of single-mode optical fiber, using a narrow bandwidth laser and by tracking the wavelength of the longitudinal mode. The fiber loop has a mode structure dependent on the length of the loop and the diameter of the core. The wavelength position of each mode depends on the refractive index of the waveguide material; therefore, changes in the refractive index may be tracked by monitoring the emitted intensity together with the phase angle as a function of wavelength.

In another embodiment, the fiber loop is adapted for measurement of forces (e.g., stress) and/or physical factors (e.g., temperature, pressure) that result in deformation (e.g., strain) of the fiber, by measuring the effect of such deformation on one or more optical properties of the fiber. Deformation, such as bending of the fiber, may alter one or more optical properties, with a smaller radius of bend associated with greater changes in the optical properties of the fiber. For example, a portion of the fiber maybe interfaced with suitable hardware so as to provide a mechanical strain sensor, as exemplified below.

The contents of all cited references are incorporated herein by reference in their entirety.

The invention is further described by way of the following non-limiting examples.

WORKING EXAMPLES

Example 1

Phase Shift Fiber Loop Spectroscopy

Introduction

Phase shift optical loop spectroscopy uses an intensity-modulated light source to pump the optical loop. This modulated pumping results in a time-varying light intensity in the optical loop, and hence the amount of light scattered from the fiber is also modulated in time. As will be shown below, the modulation frequencies of the incoming and emitted light are identical and the phase angle between the modulated pumping light signal and the light scattered from the fiber provides an accurate measure for the optical loss in the loop, without the need for extended averaging and exponential fitting.

In these phase-angle ring-down measurements, a continuous wave (cw) laser beam is intensity modulated in time. This can be done either internally or externally by an electro-optical modulator. The time dependence of incoming intensity is $$I_{in} = I_0[1 + \alpha \sin(\Omega t)] \quad (1)$$

where $\alpha \leq 1$ is the modulation depth and $\Omega = 2\pi f$ is the angular modulation frequency.

When such a modulated beam is injected into the loop, the energy density in the loop, and hence the light intensity emitted by or scattered from the loop will be modulated with the same frequency, $\Omega$, but will be phase shifted with respect to the input signal (Engeln et al., 1996).

In Equation (2)

$$I(t) = \frac{1}{\tau}\int_0^t I_0[1 + \alpha\sin(\Omega t')]\exp\left(-\frac{t-t'}{\tau}\right)dt' \quad (2)$$

$$= I_0\left\{1 + \frac{\alpha}{\sqrt{1+\Omega^2\tau^2}}\sin[\Omega t - \arctan(\Omega\tau)]\right\}$$

where $\tau$ is the ring-down time of the cavity, it is assumed that the transit time of light in the cavity is short compared to the ring-down time and the modulation period. From the above equation, the phase shift $\phi$ can be given as $$\phi = -\arctan(\Omega\tau) \quad (3)$$

and the modulation depth of the emitted light is $$\alpha' = \frac{\alpha}{\sqrt{1+\Omega^2\tau^2}} \quad (4)$$

While the ring-down time can in principle be determined from either the modulation depth or the phase shift; only phase shift measurements have the potential to yield comparable sensitivity, detection limit, and time response to conventional time-resolved ring-down spectroscopy.

Methods

The experimental setup consisted of a laser diode (JDS Uniphase SDL-2372-P1, 810 nm±3 nm, max. 2 W) current-modulated at frequencies around 200 kHz. The laser output was delivered by 1 m of multimode fiber which was coupled to the fiber-loop (Fiber-Tech, Optica, AS400/440IRPI, 26 m) with the aid of a drop of dimethylsulfoxide (DMSO). The coupling efficiency of such an arrangement is low (~$10^{-5}$), but can readily be improved using commercial fiber-fiber couplers if necessary. A photomultiplier tube (PMT; Hamamatsu 950) was placed at a different location along the loop and monitored the light intensity in the loop by detecting photons scattered from the fiber core and cladding. In preliminary experiments the ends of a 400/440 µm optical fiber were coupled using an x-y-z translation stage to form a loop with low optical losses. The gap between the fibers was filled with either water or DMSO containing variable amounts of dye. Since the refractive index of DMSO (n=1.4787) is close to the refractive index of the fiber core (n=1.457), the solvent acted as index-matching fluid and nearly eliminated the back reflection at the fiber-solution interface. The lower refractive index of water had a surprisingly small effect on the coupling efficiency between the fiber ends, possibly due to a focussing effect at the fiber-water interface. The alignment was optimized and characterized using a microscope.

The PMT signal was fed into a fast lock-in amplifier (Stanford Research Systems SR 844) and referenced to the driving current of the laser diode. To reduce radio frequency interference, all the cables were shielded. The size of the gap between the fiber ends was adjusted to about 10% of the diameter of the fiber core and was experimentally determined to be about 42 µm.

To get the highest sensitivity in the phase-angle measurement, the angular modulation frequency was set to around $\Omega = 1/\tau$, i.e., to a phase angle of about $\phi = 45°$ (see Equation 3). Due to the inherent time delays in cables and electronic components, an offset phase angle was determined. This was easily be done by phase angle measurements obtained using different concentrations of DDCI analyte as described below, or by determining the relative phase as a function of the modulation frequency $\Omega$. The standard deviation of phase angle measurement depended strongly on the readout rate and the intensity of the photon signal and was typically around 0.05 degrees. It was ultimately restricted by the instrumental limit of the lock-in amplifier (which in the present case was 0.02° according to the manufacturer's specifications).

In the capillary electrophoresis measurements the fiber ends were joined by a commercial 4-way microcross (Upchurch Scientific) instead of the translation stage. In the microcross, the two fiber ends (100/140 µm Fiber Tech Optica AS100/140IRA) were inserted through opposing holes (150 µm) and the capillary ends (Polymicro Technologies 100/360 µm) were inserted through the other two holes. In this experiment the modulation frequency was 150 kHz, the length of the fiber loop was about 65 m, and the size of the gap between the fiber ends was calculated to be 31 µm.

Results

Figure 2:
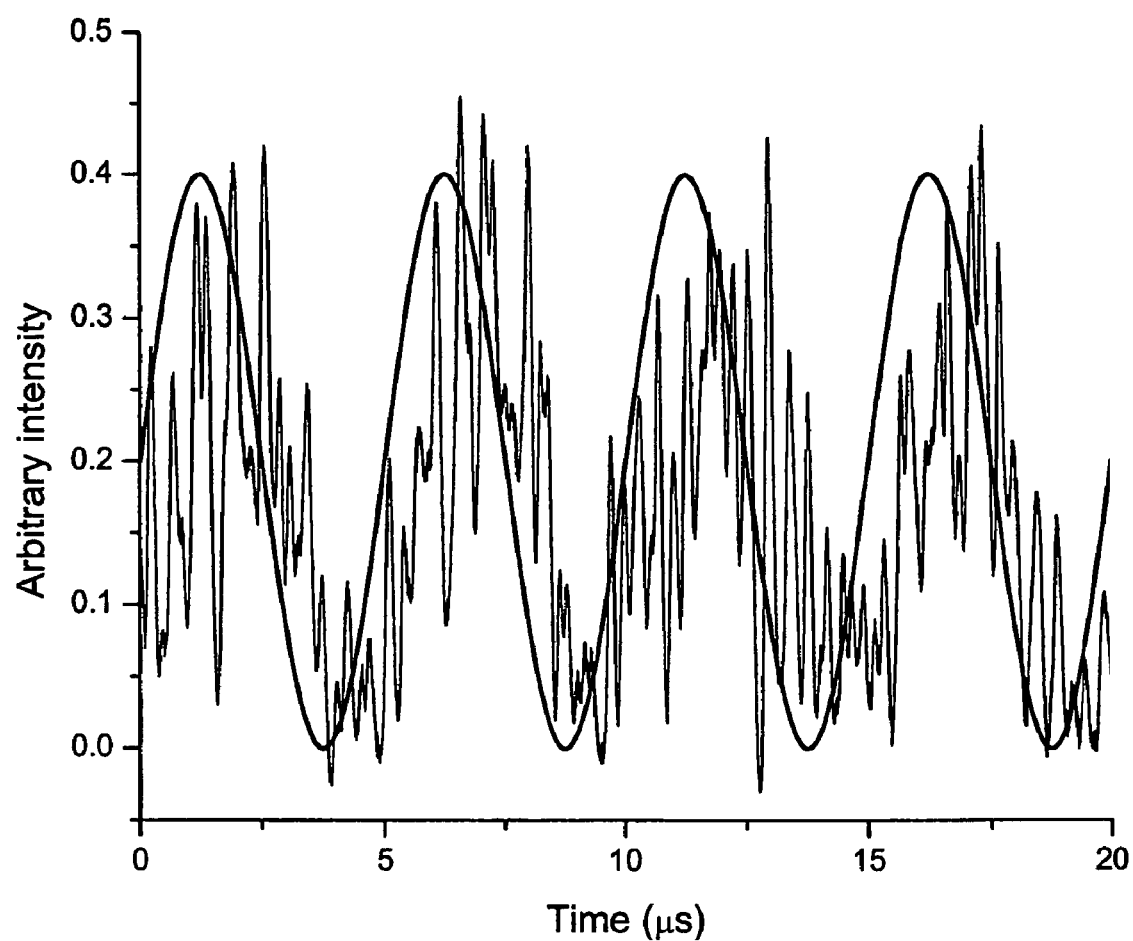
FIG. 2 is a plot showing a phase shift of the optical signal relative to the (smooth) reference signal from the function generator, for the setup shown in FIG. 1.

FIG. 2 shows a typical trace of the time dependence of the intensity detected by the PMT. A driving voltage modulated at 200 kHz was supplied to the laser diode and also used as a reference signal. The reference is shown as a solid curve and the phase shift of the emitted light can be easily seen. The transient signal and reference were connected to the lock-in amplifier, which averaged the phase angle measurement over a period of 100 ms (variable from 1 ms to 1 s).

When the clear DMSO solvent was replaced with a solution of DDCI in DMSO at different concentrations, the phase angle was used to determine the ring-down time and hence the absorption in the sample. DDCI is not optically stable and its absorption band will shift into the visible region after prolonged exposure to the light. Therefore the phase-angle averages of only the first 20 s were used in FIG. 3.

As mentioned above, there exists an offset to the phase angle arising from inevitable time-delays in the electronic signal transmission in the electronic components, the cables, and the laser diode, as well as light transmission in the power delivery fiber. This offset can readily be accounted for by introducing the offset angle, $\phi_0$, into Equation (3), resulting in $$\phi_m = \phi_0 - \arctan(\Omega\tau) \quad (5)$$

where $\phi_m$ is the phase angle measured by the lock-in amplifier. Substituting the photon lifetime (Brown et al., 2002)

$$\tau = \frac{L}{c_0(-\ln(T_{sp}) + \alpha L + \varepsilon_{DMSO}d + \varepsilon_{DDCI}Cd)} \quad (6)$$

into Equation (5), one obtains $$\phi_m = \phi_0 - \arctan\frac{\Omega L}{c_0(-\ln(T_{sp}) + \alpha L + \varepsilon_{DMSO}d + \varepsilon_{DDCI}Cd)} \quad (7)$$

Here $\varepsilon_{DDCI} = 3.343 \times 10^5$ (M cm)$^{-1}$ is the extinction coefficient of DDCI (given with respect to base e) at its peak absorption wavelength of 825 nm, $C_{DDCI}$ is its concentration (M), and d is the width of the cavity formed by the two fiber ends. A similar term is introduced to account for the absorption of the solvent.

To simplify the model one can combine the optical loss from the splice alignment, the absorption of the fiber and the solvent into a single expression $A_0$. This term represents all optical loss processes other than the analyte's absorption and is constant for a given flow system.

$$\phi_m = \phi_0 - \arctan\frac{\Omega L}{c_0(A_0 + \varepsilon Cd)} \quad (8)$$

As can be seen from Equation (8), the phase angle dependence on concentration is not linear. An advantage of this non-linearity is that phase-angle measurements are more sensitive at low concentrations. The offset angle $\phi_0$ can be determined from a linear fit using Equation (8) and the fact that $-\text{ctan}(\phi_m - \phi_0)$ is proportional to the concentration. Eventually, this procedure will be done when calibrating the detector. For small concentrations, the determination of the offset angle is not necessary since $\phi_m$ changes approximately linearly with concentration.

In Equation (8), only $\phi_0$, $A_0$, and d were unknown and were determined by fitting (FIG. 3) to give $\phi_0 = -36.3°$, $A_0 = 0.60$, and d=42 μm. For a 26.4 m fiber loop, the ring-down time of $\tau = 224$ ns without DDCI is therefore much shorter than expected for the light decay in the fiber core ($\tau \sim 1$ μs), which implicates that the detected photons were scattered not only from the fiber core, but also from the fiber cladding. Furthermore, high-order core and cladding modes, which were biased against in previous pulsed fiber loop ring-down spectroscopy (FLRDS) experiments by gating the detector (Brown et al., 2002), gave rise to strong and fast intensity decays within the first 100 ns.

Because the lock-in amplifier can only provide one averaged phase angle, measurements at a number of modulation frequencies need to be made to characterize the components associated with the different optical decay processes. However, since one needs to Fourier transform these frequency domain measurements in real time, the time-resolution of the measurement is affected in an on-line detector. A simpler way to solve the problem of multiple optical decays with different time constants is to increase the length of the fiber loop and thereby enhance the relative losses of the high-order modes and cladding modes over the long-lived low-order core modes.

Figure 4:
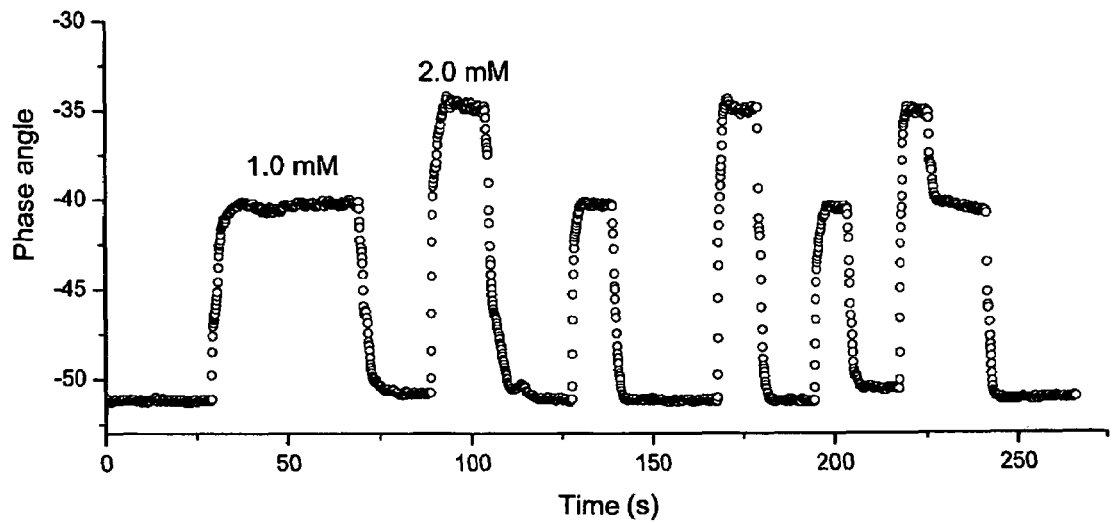
FIG. 4 shows a plot of phase angle vs time for 1.0 and 2.0 mM solutions of DDCI dye placed between two ends of a fiber, forming a fiber loop. The solutions were rapidly exchanged and the phase angle was measured. Measurements were taken every 100 ms and the time resolution of the measurement was sufficient to monitor the time taken for the solution to be completely replaced.

FIG. 4 is a demonstration of the greatly increased time-response of the phase shift FLRDS (PS-FLRDS) system over pulsed FLRDS. Here, drops of DDCI with different concentration were added alternately with pure DMSO solvent between the two fiber ends. The rapid change in phase angle between −52 deg to −40 deg and −35 deg was used together with the calibration of FIG. 4 to obtain quantitative and time-resolved concentration transients. From the figure the time response was obtained from the onset of the leading edge of each peak, and was better than 200 ms. We consider this a lower limit since the time needed to displace the existing solution is on a similar timescale and may determine the time resolution one can obtain in this experiment.

Figure 3:
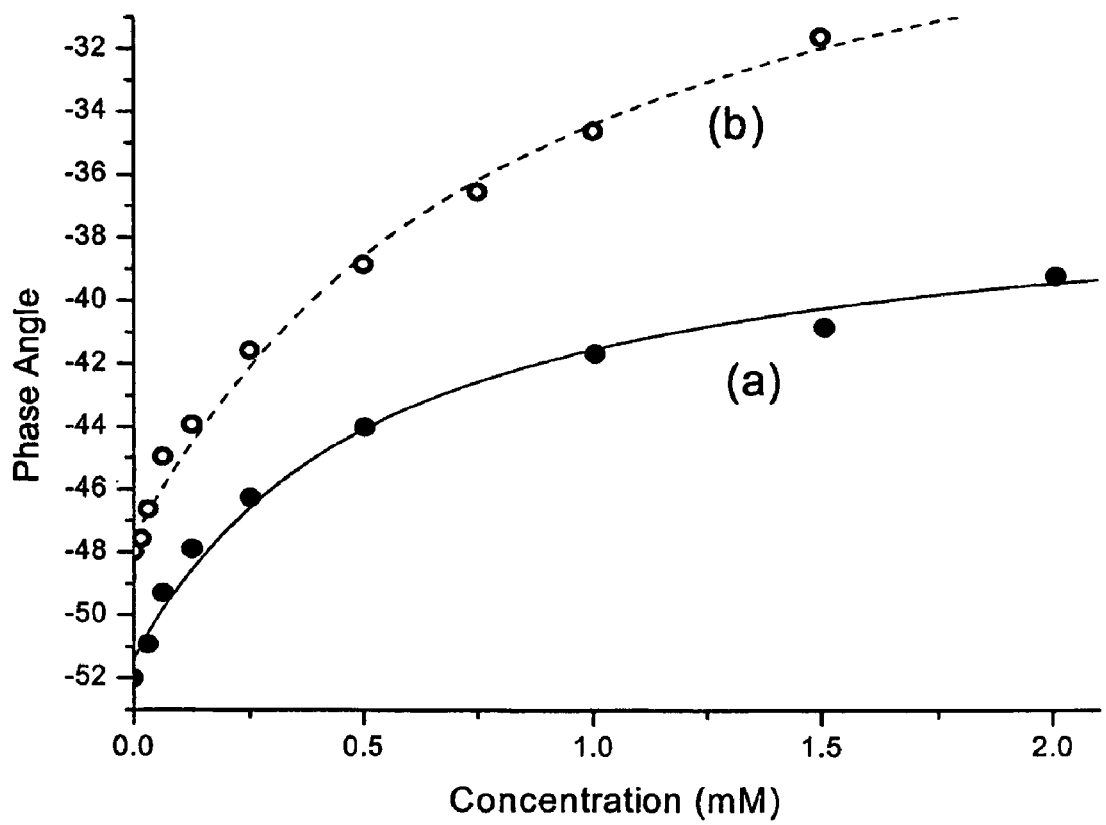
FIG. 3(a) shows a plot of phase angle as a function of concentration for a 26.4 m fiber loop, used to determine a phase angle difference of $\phi_0 = -36.3°$, absorption $A_0 = 0.60$ in absence of 1,1'-diethyl-4,4'-dicarbocyanine iodide (DDCI) dye, and gap between the fiber ends of $d=42$ μm; (b) shows concentration dependence of phase angle in capillary electrophoresis using a microcross. Here, $\phi_0 = -23.3°$, $d=31$ μm and $A_0 = 0.66$ were determined from the fit for a $L=65$ m fiber loop.

For the capillary electrophoresis experiment a microcross was used to couple the fiber ends, and the concentration dependence of phase angle is shown in FIG. 3. A fit of the experimental data using Equation (8) yielded $A_0 = 0.66$, $\phi_0 = -23.3°$, and d=31 μm. The background optical transmission, $A_0$, was slightly higher compared to the value of $A_0 = 0.66$ for the 400/440 μm fiber experiment, indicating that one can achieve fair fiber-fiber coupling efficiencies with a simple and inexpensive commercial microcross.

Figure 5:
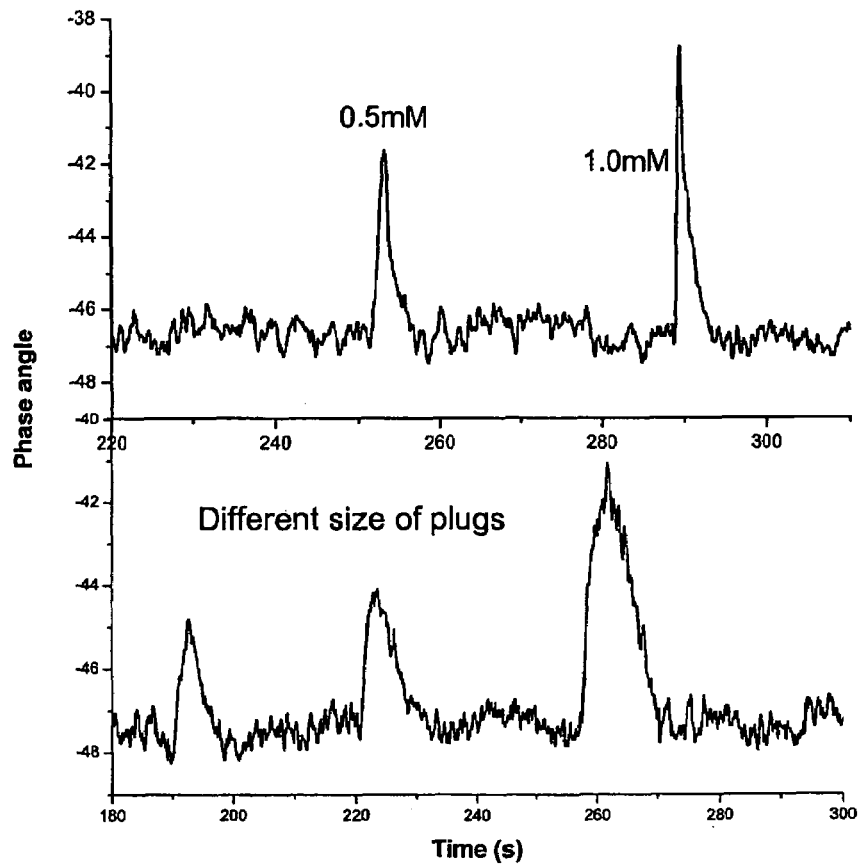
FIG. 5 is a plot of phase angle vs time showing transient absorption peaks due to absorption of DDCI in dimethylsulfoxide (DMSO), recorded by pushing the analyte through a 100 μm capillary using a syringe: the upper panel shows peaks at two concentrations; and the lower panel shows peaks for three different lengths of plugs of a 1 mM solution. There is significant peak broadening because of the large size of the capillary (100/360 μm).
Figure 6:
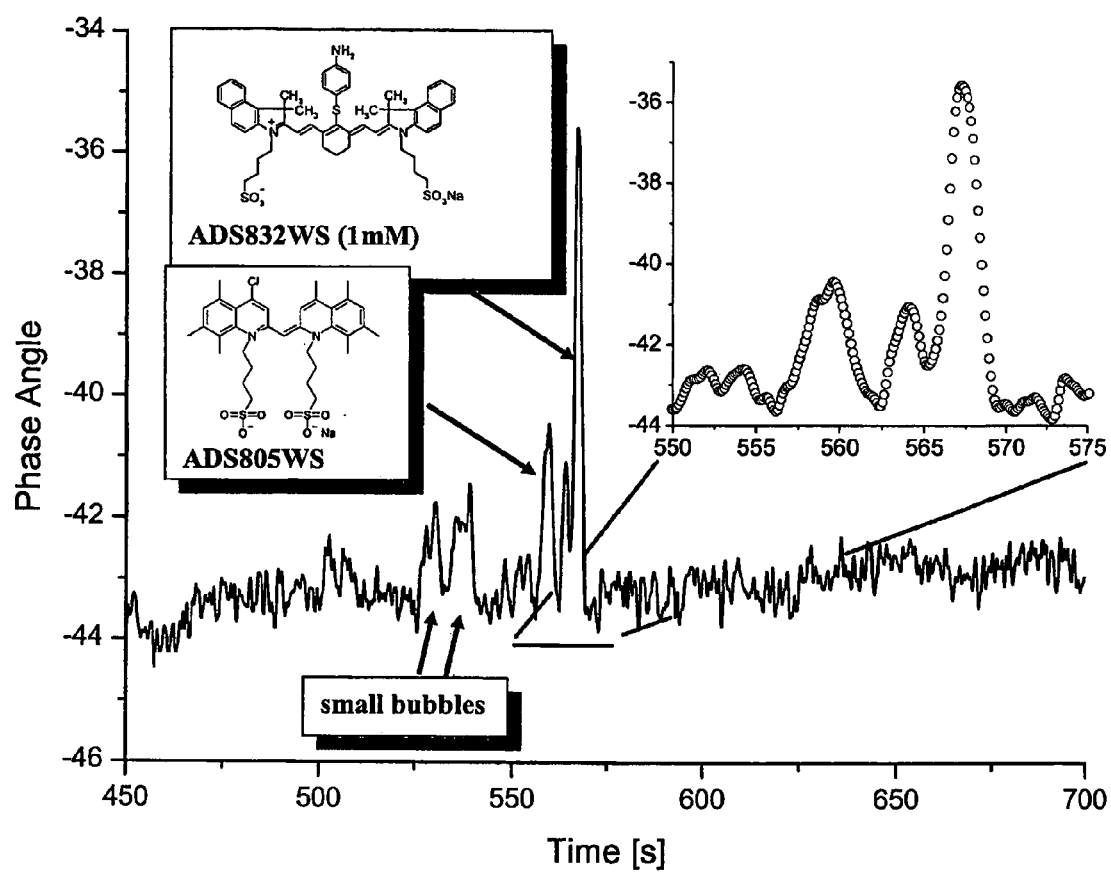
FIG. 6 is a plot showing capillary electrophoresis separation of two dyes, ADS 805 WS and ADS 830 WS dissolved in water (buffered by $KH_2PO_3$, pH~8.0). 4.5 kV was used to elute the mixture.

To test the capabilities of FLRDS in a more realistic analytical environment, a fast transient peak was obtained in two ways. First a syringe was used to inject the solution into the capillary, and FIG. 5 shows the measured change of phase angle when two different concentrations and different sizes of plugs of solution were used. Secondly, a capillary electrophoresis separation of two dyes, ADS805WS and ADS830WS (American Dye Source, Inc., chemical formulae $C_{36}H_{44}ClN_2O_6S_2Na$ and $C_{46}H_{51}ClN_2O_6S_2$, respectively) was undertaken, and resulted in an electrochromatogram that shows the retention times of not only the original dyes, but also of the degradation products (FIG. 6).

Discussion

To determine the detection limit, the derivative of Equation (8) was calculated as follows:

$$\left.\frac{d\phi}{dC}\right|_{C=0} = \frac{\Omega L \varepsilon d c_0}{c_0^2 A_0^2 + \Omega^2 L^2} \quad (9)$$

If the detection limit (DL) is defined as $3\theta_c$, then $$DL = \frac{c_0^2 A_0^2 + \Omega^2 L^2}{\Omega L \varepsilon d c_0} 3\sigma_\phi \quad (10)$$

For an uncertainty in the phase angle measurement of $\theta_\phi = 0.05°$, a detection limit of 6 μM was calculated. This value is comparable to the lowest concentrations of 30 μM and 15 μM shown in FIG. 4. Given the sample volumes of 5 nL and 240 pL respectively, these concentrations correspond to 150× $10^{-15}$ mol and 3×$10^{-15}$ mol, respectively. PS-FLRDS thus enables absorption detection of about 2 billion molecules within about 100 ms.

A number of improvements can be made to lower the detection limit. The accuracy of phase angle measurements affects the detection limit. $\theta_\phi$ is mainly decided by the amount of signal fed into the lock-in amplifier as determined by the coupling efficiency. Improving the signal fraction from the core over the cladding modes increases $A_0$, whereas tuning to the peak absorption wavelength ($\epsilon$) of the analyte and optimizing the gap size, d, and fiber length, L, further helps to achieve a lower detection limit.

The data collection rate was 10 Hz and the time constant of the lock-in amplifier was therefore set to 100 ms. Should it be required one can work at considerably higher readout rates—limited ultimately by the modulation frequency to 10 μs—but for microfluidic devices, a data acquisition rate of 10-100 Hz is sufficient to distinguish the transient peaks.

We note that many of the disadvantages of phase shift CRDS measurements do not play a large role in PS-FLRDS. While the effective ring-down time (RDT) is an average of the RDTs in the fiber core and cladding, and therefore considerably smaller than that expected from RDT in the fiber core only, its change with concentration is predictable and can be understood using Equation (6). Furthermore, since a large number of modes is excited in a multimode fiber, one does not need to be concerned with mode-beating or mode-build-up effects. Finally, FLRDS is not so much a tool for the measurement of very weak (strongly forbidden) transitions or for extremely dilute samples as for the determination of sub-millimolar concentrations in small liquid samples. In this application one would use a calibration curve together with an independent measurement of the absorption cross section in a large sample to determine the concentration. Therefore, a possible inaccuracy in the effective ring-down time would be corrected for using the phase shift technique of the invention.

CONCLUSIONS

In a conventional pulsed laser (10-100 Hz) FLRDS measurement, one ring-down time measurement takes about 30-100 s while the effective data acquisition takes only a small fraction of that time. PS-FLRDS improves the duty cycle and data acquisition rate, and thus enables real-time measurements in analytical environments. As demonstrated above, PS-FLRDS is suitable as an online absorption detector for capillary electrophoresis with time resolution of 10-100 ms and detection limit in the micromolar concentration range.

PS-FLRDS is compact and inexpensive. In principle, one could integrate all electronic components, i.e., the function generator, diode laser driver, photodiode circuit, and phase-detector into a single board with a computer interface, thereby reducing radio frequency interference an improving performance. PS-FLRDS is also robust and sensitive. The quasi-continuous measurement of the phase angle eliminates software averaging and exponential fitting, but does not permit a separate characterization of the competing optical loss processes. While this did not pose an immediate problem in this example, fast optical decays in cladding modes and lossy core modes will have to be dealt with as the detection limit of FLRDS is reduced. Commercial fiber-fiber couplers can be used to deliver the light signal into the optical loop as well as for detection of its intensity in the loop. They will likely reduce the fraction of light travelling through cladding modes, and with higher coupling efficiencies also increase the accuracy with which the phase angle can be measured.

In certain applications absorption detection at wavelengths shorter than 300 nm may be desired; however, transmission of commercial fibers is greatly reduced at wavelengths shorter than 600 nm. Example 2 illustrates an experimental arrangement that conceptually permits FLRDS detection of molecules in the spectral region used for telecommunications. At about 1.6 μm optical waveguides have good transmission, and many biological molecules show absorption bands due to vibrational overtone transitions in this frequency range, which may be interrogated using FLRDS.

Example 2

Near Infrared Phase Shift Optical-Loop Measurement of Optical Losses

Introduction

In the fiber loop measurement scheme described in Example 1, there is a limit in the spectral range to which the technique may be applied. This limit is given by the use of the optical waveguide combined with the photomultiplier detector. The absorption spectrum of a typical fiber optic waveguide has a maximum transmission centered around two spectral regions near 1.35 μm and 1.5 μm, which are separated by a strong absorption peak due to excitation of OH overtone vibrations in the waveguide material. A third transmission window exists near 800 nm. The transmission then decreases dramatically as the wavelength of the guided wave is decreased from the near infrared (NIR) through the visible region into the ultraviolet (UV). In example 1 the photodetector was a photomultiplier tube with a detection efficiency whose wavelength dependence is the inverse of the fiber transmission curve. The detector was most sensitive in the UV and visible region, with decreasing sensitivity in the near IR, until at about 850 nm the detection efficiency decreased to near zero. The combination of these two wavelength response curves limits the experiment to a wavelength window from about 780 nm to about 830 nm, and consequently many experiments to date have been conducted on sample dyes that show strong absorption features in this spectral region.

Figure 7:
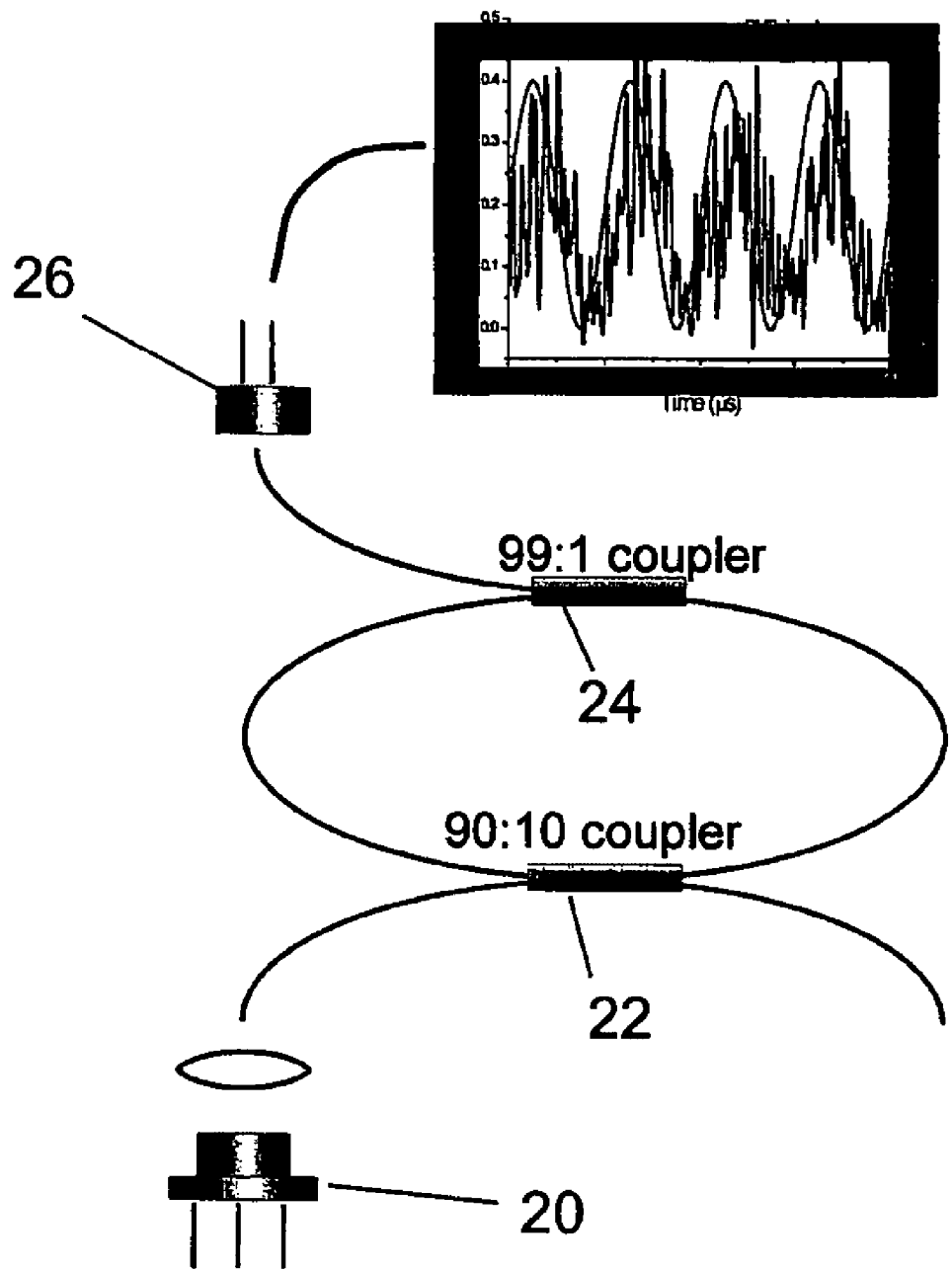
FIG. 7 is a schematic diagram of an experimental setup used to investigate optical losses of a fiber optic cable in the 1.55 μm wavelength region by determining optical losses of radiation travelling through the fiber core independently from the losses by the cladding.
Figure 8:
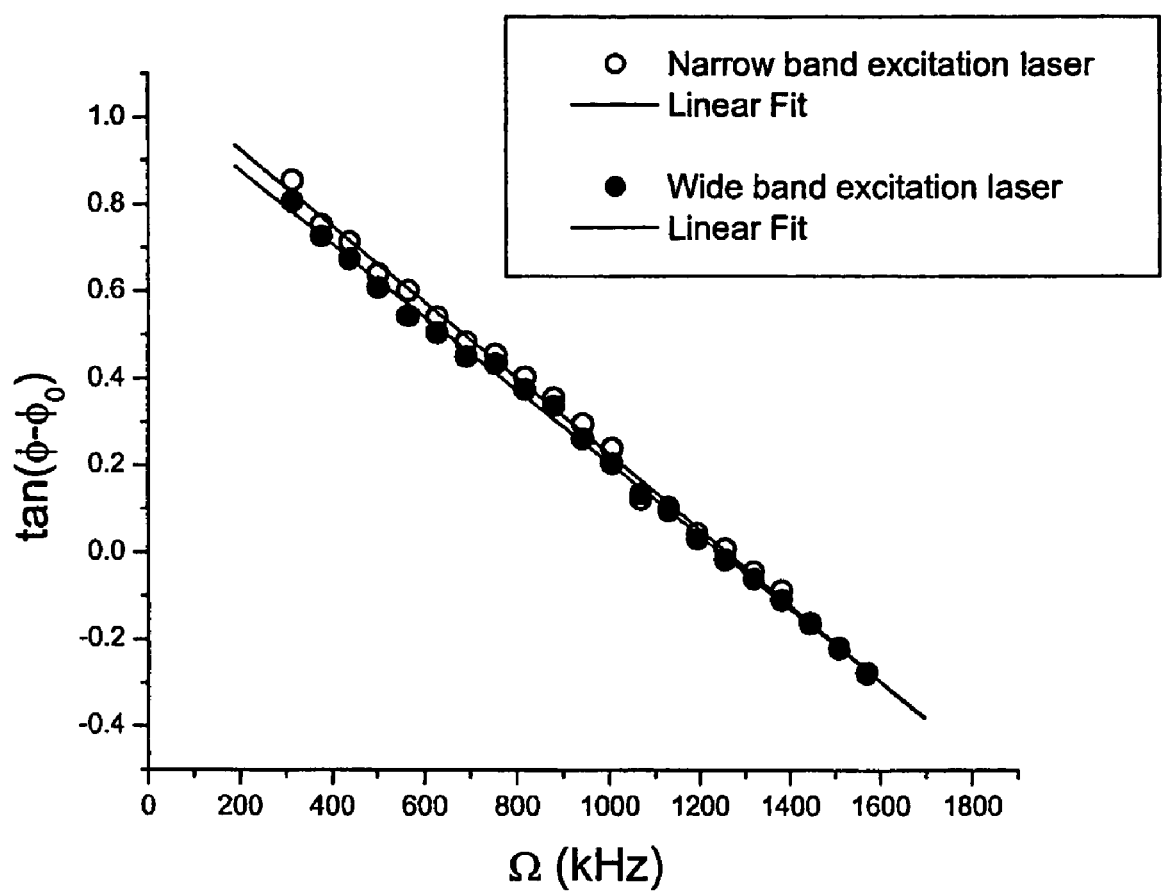
FIG. 8 is a plot of the phase angle $\phi$ as a function of the angular modulation frequency $\Omega$ using the setup shown in FIG. 7, for broadband and narrow band excitation sources. The optical decay constant $\tau$ and the offset phase angle $\phi_0$ were determined from the slope.

In this example an alternative excitation source and photodetector were used to exploit the much higher optical transmission of the fiber optic cable in the 1.55 μm wavelength region. As shown in FIG. 7, using a tunable (1.5-1.62 μm) NIR laser source 20 (ANDO), single mode fibers (Fiberguide), directional couplers 22, 24 (SENKO and Fiber metric), and either an In—Ga—As photodiode 26 (Thorlabs) or an optical spectrum analyser (Agilent 86142B), a 4 m fiber loop setup was realized, which enabled the determination of optical losses of radiation travelling through the fiber core independently from the losses by the cladding. The phase angle $\phi_m$ was measured as a function of the angular modulation frequency $\Omega$ of a broadband excitation source ($\Delta\nu=200$ MHz), and the optical decay constant $\tau=840$ ns and the offset phase angle $\phi_0=44°$ were determined from the slope (FIG. 8). When using a narrow band light source ($\Delta\nu=200$ kHz) the resultant numbers were very similar, indicating that the longitudinal mode structure in the fiber loop was either fluctuating very quickly and/or that the mode spacing was small. Note that in both experiments a 90:10 X-coupler was used to introduce light into the loop and a 99:1 tap was used to direct light out of the loop. Despite the fact that these optical devices have inherent losses and that the two fusion splices by which they were connected into the loop also had optical losses, the loss per pass was calculated to be below 3%.

Similar experiments using a 99:1 X-coupler and 99:1 tap in a much shorter loop of only L=1 m gave lower losses of only 0.7% (0.032 dB) per pass, indicating that there is a considerable amount of intensity build-up in the loop and also a higher than expected optical finesse.

An experimental arrangement such as this therefore allows for very accurate determination of optical losses in single mode optical devices such as, for example, Bragg gratings, couplers, and splices. In addition, the inventors contemplate introducing into the loop optical devices whose optical loss characteristics are modified as a function of their environment, so as to measure and monitor environmental variables, for example. Environmental variables that could be interrogated by such a loop include, but are not limited to, temperature (e.g., as it affects the transmission/reflection characteristics of a Bragg grating), strain on the fiber, absorption spectrum of the evanescent wave, and refractive index of a surrounding medium. We note that wavelengths around 1.5 μm are particularly suited for unspecific detection of many organic molecules through the vibrational overtone absorption bands of the CH, NH and OH stretching vibrations.

Example 3

Use of PS-FLRDS as a Fiberoptic Sensor for Mechanical Strain

Figure 9A:
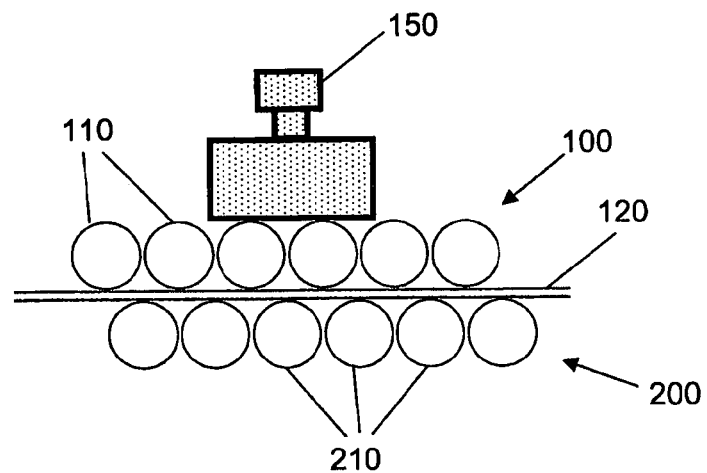
FIG. 9A is a schematic diagram of a fiber-optic strain sensor according to the invention.

An experimental setup similar to that described in Example 2 was used to investigate the effect of deformation on the optical waveguide loop. A 10 m loop of 125 μm single mode fiber (Fiberguide) was formed by splicing the fiber ends using a fusion splicer. Using a tunable (1.5-1.62 μm) NIR laser source (ANDO) which was coupled into the loop using a 99.5:0.5 directional coupler (Lightel), and an inline power monitor (EigenLight M160) connected to a lock-in amplifier, optical losses of radiation traveling through the fiber core were determined independently from the losses caused by the cladding. The phase angle $\phi_m$ was measured at a fixed angular modulation frequency $\Omega$ of a broadband excitation source ($\Delta v$=200 MHz). Note that in this experiment a 99.5:0.5 X-coupler was used to introduce light into the loop which was detected by the inline power monitor contained within the fiber loop. Additional loss was introduced by bending a section of the waveguide loop using a custom made strain sensor. As shown in FIG. 9A, the strain sensor consisted of a sandwich of two parallel arrays 100, 200 of cylinders 110, 210, each cylinder being about 12.5 mm in diameter, arranged such that the longitudinal axes of the cylinders of the two arrays were parallel but offset, and the optical fiber. The fiber 120 was placed between the arrays perpendicular to the longitudinal axes of the cylinders. Compressing the waveguide between the two arrays caused the fiber to bend in a periodic nature as set by the size and spacing of the cylinders, and with a bending radius that depended on the force applied to the cylinder arrays. Impulse (time) response of the strain sensor was determined by dropping a 200 g weight 150 from a height of 3 cm onto the sensor.

Figure 9B:
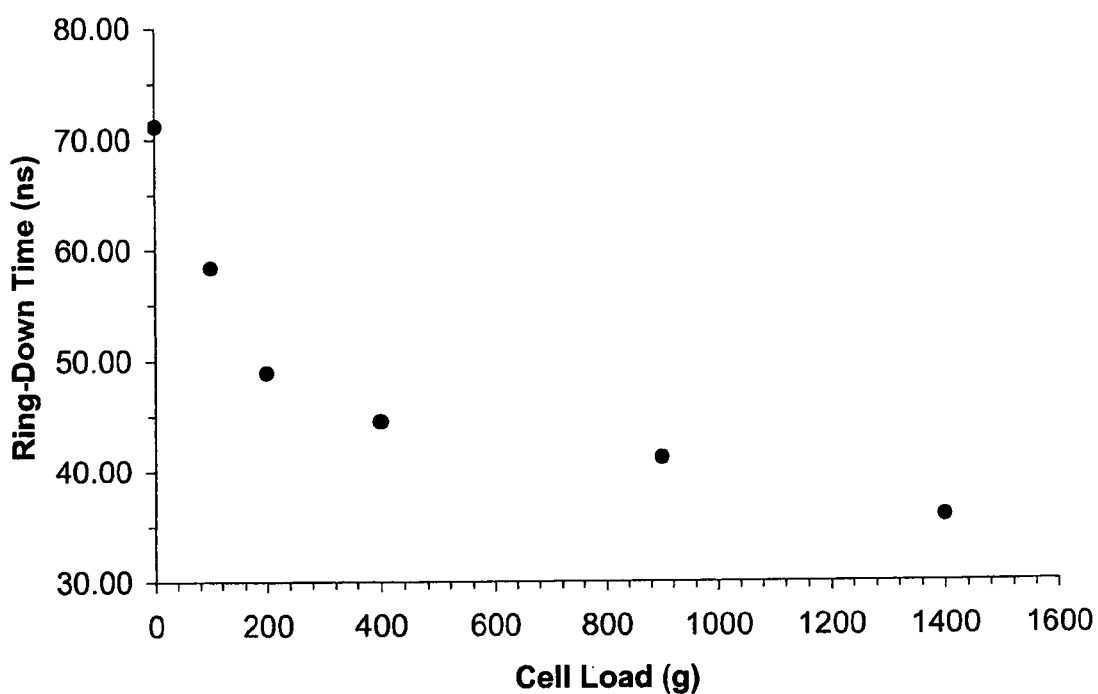
FIG. 9B is a plot of the phase angle as a function of the load on the fiber-optic strain sensor of FIG. 9A
Figure 9C:
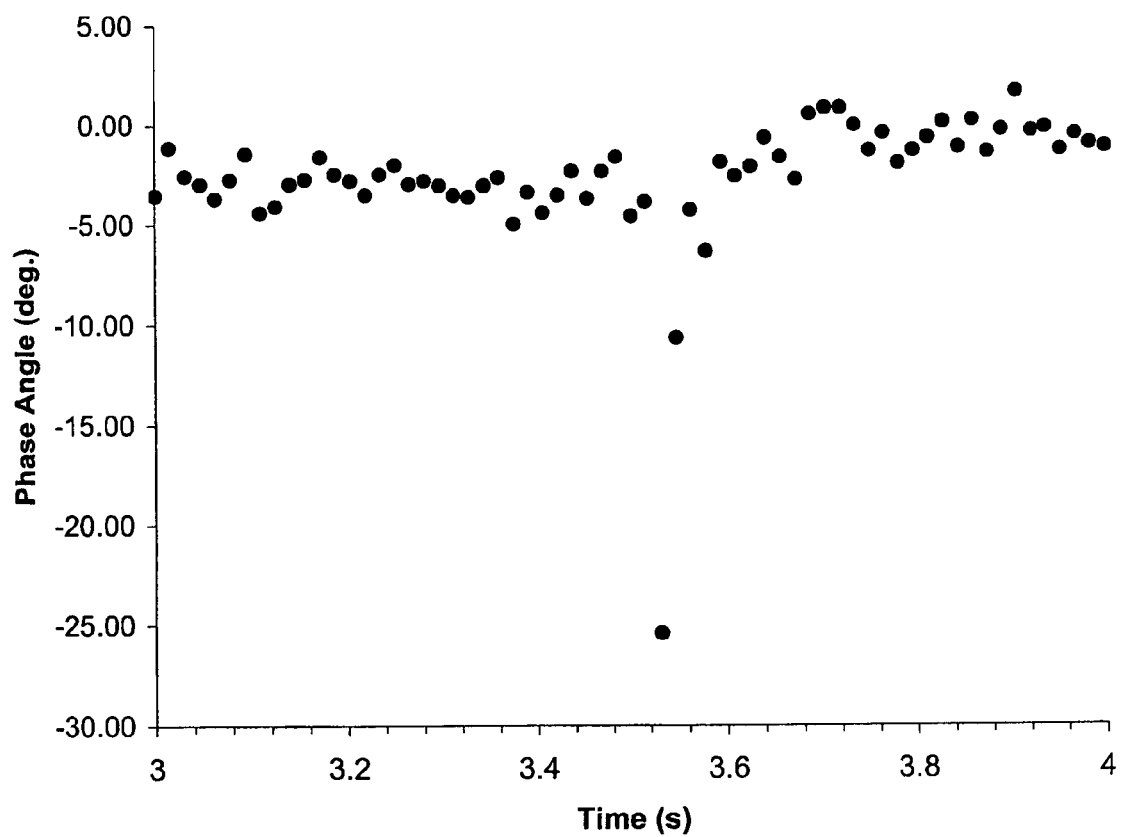
FIG. 9C is a plot showing the time response of the fiber-optic strain sensor of FIG. 9A.

The ring-down time (phase angle) and impulse (time) response of the strain sensor are shown in FIGS. 9B and 9C, respectively. In particular, FIG. 9B shows that ring-down time decreased with increasing load, indicating that the optical loss increased with increasing deformation of the fiber. The minimum time response of the measurement was 10 ms, set by the 100 Hz data acquisition rate used. From FIG. 9C it can be seen that the response time of the device is not longer than this lower measurement limit.

Those skilled in the art will recognize, or be able to ascertain using routine experimentation, variations of the embodiments and examples described herein. Such variations are intended to be within the scope of the invention and are covered by the appended claims.

REFERENCES

Berden, G.; et al., 2000, Cavity ring-down spectroscopy: Experimental schemes and applications, *International Reviews in Physical Chemistry* 19:565.

Brown, R. S.; et al., 2002, Fiber-loop ring-down spectroscopy, *J. Chem. Phys.* 117:10444.

DeMille, S.; et al., 2002, Comparison of CRDS to ICL-PAS and phase-shift CRDS spectroscopies for the absolute intensities of C—H (? $V_{CH}$=6) overtone absorptions, *Chem. Phys. Lett.* 366:383.

Engeln, R.; et al., 1996, Phase shift cavity ring down absorption spectroscopy, *Chem. Phys. Lett.* 262:105.

Hallock, A. J.; et al., 2002, Direct monitoring of absorption in solution by cavity ring-down spectroscopy, *Anal. Chem.* 74:1741.

Jakubinek, M.; et al., 2004, Configuration of ring-down spectrometers for maximum sensitivity, *Can. J. Chem.* 82:873.

Lewis, E.; et al., 2001, Phase shift cavity ring-down measurement of C—H (? v=6) vibrational overtone absorption, s *Chem. Phys. Lett.* 334:357.

Polynkin, P.; et al., 2004, Efficient and scalable side pumping scheme for short high-power optical fiber lasers and amplifiers, *IEEE Photonics Technology Letters* 16:2024.

Romanini, D.; et al., 1993, Ring-down cavity absorption spectroscopy of the very weak HCN overtone bands with six, seven, and eight stretching quanta, *J. Chem. Phys.* 99:6287.

Scherer, J. J.; et al., 1997, Cavity ring-down laser absorption spectroscopy: History, development, and application to pulsed molecular beams, *Chemical Reviews* 97:25.

Stewart, G.; et al., 2001, An investigation of an optical fibre amplifier loop for intra-cavity and ring-down cavity loss measurements, *Meas. Sci. Technol.* 12:843.

von Lerber, T.; et al.; 2002, Time constant extraction from noisy cavity ring-down signals, *Chem. Phys. Lett.* 353:131.

Xu, S.; et al., 2002, Cavity ring-down spectroscopy in the liquid phase, *Rev. Sci. Instr.* 73:255.

We claim:

1. An apparatus for measuring one or more optical properties of a test medium, comprising:
    a passive optical waveguide loop that provides a continuous path for a light signal launched into the loop to travel around the loop repeatedly, the loop adapted to accept a test medium such that the light signal traveling around the loop interacts with the test medium each time the light signal travels around the loop;
    an intensity-modulated light source for illuminating the loop with a light signal at an intensity modulation envelope reference phase;
    a detector for detecting a phase of the intensity modulation envelope of said light signal along the loop; and
    an analyzer for comparing the detected phase of the intensity modulation envelope of the light signal with the reference phase of the intensity modulation envelope of the light signal;
    wherein a result of the comparison is indicative of one or more optical properties of the test medium.

2. The apparatus of claim 1, further comprising a device for displaying and/or storing and/or manipulating data corresponding to at least one of said reference phase, said detected phase, and said comparison.

3. The apparatus of claim 1, wherein the optical waveguide is an optical fiber.

4. The apparatus of claim 1, wherein the waveguide loop is the test medium.

5. The apparatus of claim 1, further comprising a capillary channel for guiding the test medium to said light.

6. The apparatus of claim 1, wherein the test medium is exposed to an evanescent wave of light that is guided by the optical waveguide loop.

7. The apparatus of claim 6, wherein the optical waveguide loop comprises a cladding, and the test medium is in the cladding.

8. The apparatus of claim 1, wherein the optical property is absorbance.

9. The apparatus of claim 1, wherein the light has a wavelength selected from about 200 nm to about 2000 nm.

10. The apparatus of claim 1, wherein the apparatus comprises a microfluidic device.

11. The apparatus of claim 1, wherein the optical waveguide loop comprises a single-mode optical fiber.

12. The apparatus of claim 1, wherein the optical waveguide loop comprises a grating.

13. The apparatus of claim 1, wherein the test medium comprises a mechanical sensor for sensing a mechanical force, and the one or more optical properties of the test medium provide information about the mechanical force sensed by the mechanical sensor.

14. The apparatus of claim 13, wherein the mechanical force is selected from stress and strain.

* * * * *